(12) United States Patent
Sunami et al.

(10) Patent No.: US 10,513,683 B2
(45) Date of Patent: Dec. 24, 2019

(54) STRUCTURE USED FOR ANIMAL CELLS, METHOD OF SEPARATING ANIMAL CELLS, AND METHOD OF ADJUSTING ELASTICITY OF SURFACE OF STRUCTURE USED FOR ANIMAL CELLS

(71) Applicant: Japan Science and Technology Agency, Kawaguchi-shi, Saitama (JP)

(72) Inventors: Hiroshi Sunami, Ginowan (JP); Ikuko Yokota, Hokkaido (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 475 days.

(21) Appl. No.: 15/104,733

(22) PCT Filed: Dec. 16, 2014

(86) PCT No.: PCT/JP2014/083247
§ 371 (c)(1),
(2) Date: Aug. 2, 2016

(87) PCT Pub. No.: WO2015/093472
PCT Pub. Date: Jun. 25, 2015

(65) Prior Publication Data
US 2016/0340641 A1    Nov. 24, 2016

(30) Foreign Application Priority Data

Dec. 18, 2013   (JP) ................... 2013-261677

(51) Int. Cl.
*C12N 5/00* (2006.01)
*C12M 1/00* (2006.01)

(52) U.S. Cl.
CPC ........... *C12N 5/0068* (2013.01); *C12M 23/26* (2013.01); *C12M 47/02* (2013.01); *C12N 2535/00* (2013.01); *C12N 2539/00* (2013.01)

(58) Field of Classification Search
None
See application file for complete search history.

(56) References Cited

U.S. PATENT DOCUMENTS

| | | |
|---|---|---|
| 2007/0148762 A1 | 6/2007 | Miyake et al. |
| 2007/0190645 A1 | 8/2007 | Miyake et al. |
| 2010/0015709 A1 | 1/2010 | Rehfeldt et al. |

FOREIGN PATENT DOCUMENTS

| | | |
|---|---|---|
| JP | 11-512778 A | 11/1999 |
| JP | 11-347382 A | 12/1999 |
| JP | 2001-065617 A | 3/2001 |
| JP | 2005-229914 A | 9/2005 |
| JP | 2005-232402 A | 9/2005 |
| JP | 2011-225462 A | 10/2011 |
| JP | 2012-105609 A | 6/2012 |
| JP | 2012-126681 A | 7/2012 |
| JP | 2012-130386 A | 7/2012 |
| JP | 2013-099272 A | 5/2013 |
| JP | 2013-150648 A | 8/2013 |
| WO | 97/18244 A1 | 5/1997 |
| WO | 2005085414 A1 | 9/2005 |

OTHER PUBLICATIONS

Choi et al., Biomaterials, vol. 33, No. 29, pp. 6943-6951; 2012 (of record).*
Lu et al., Biomedical Microdevices, vol. 14, pp. 659-667; 2012 (electronically available Mar. 4, 2012) (of record).*
Georges et al., Journal of Applied Physiology, vol. 98, pp. 1547-1553 (2004) (of record).*
Ashby William J et al: "Magnetically attachable stencils and the non-destructive analysis of the contribution made by the underlying matrix to cell migration", Biomaterials, vol. 33, No. 33, Aug. 31, 2012 (Aug. 31, 2012), pp. 8189-8203, XP028938879.
Chao Pen-Hsiu Grace et al: "Micro-composite substrates for the study of cell-matrix mechanical interactions", Journal of the Mechanical Behavior of Biomedical Materials, vol. 38, Jan. 28, 2014 (Jan. 28, 2014), pp. 232-241, XP029016593.
Communication Supplementary European Search Report dated Jul. 6, 2017 in connection with European Patent Application No. 14872640.9, 8 pages.
Lo C M et al., entitled "Cell Movement is Guided by the Rigidity of the Substrate," Biophysical Journal, vol. 79, Jul. 2000, 144-152.
Jiang G et al., entitled "Rigidity Sensing at the Leading Edge through $\alpha v\beta 3$ Integrins and $RPTP\alpha$," Biophysical Journal, vol. 90, Mar. 2006, 1804-1809.
Welle A et al., entitled "Competitive protein adsorption on micro patterned polymeric biomaterials, and viscoelastic properties of tailor made extracellular matrices," Biomolecular Engineering 24 (2007) 87-91.
Lazopoulos K A et al., entitled "Durotaxis as an elastic stability phenomenon," Journal of Biomechanics 41 (2008) 1289-1294.
Fung P C W et al., entitled "Probing the mystery of Chinese medicine meridian channels with special emphasis on the connective tissue interstitial fluid system, mechanotransduction, cells durotaxis and mast cell degranulation," Chinese Medicine 2009, 4:10, 6 pages.
Isenberg B C et al., entitled "Vascular Smooth Muscle Cell Durotaxis Depends on Substrate Stiffness Gradient Strength," Biophysical Journal, vol. 97, Sep. 2009, 1313-1322.
Harland B et al., entitled "Adhesion dynamics and durotaxis in migrating cells," Phys. Biol. 8 (2011), 015011, 11 pages.
Kawano T et al., entitled "Elasticity boundary conditions required for cell mechanotaxis on microelastically-patterned gels," Biomaterials 32 (2011) 2725-2733.
Ananthanarayanan B et al., entitled "Elucidating the mechanobiology of maligant brain tumors using a brain matrix-mimetic hyaluronic acid hydrogel platform," Biomaterials 32 (2011) 7913-7923.

(Continued)

*Primary Examiner* — Soren Harward
*Assistant Examiner* — Paul D. Pyla
(74) *Attorney, Agent, or Firm* — Amster, Rothstein & Ebenstein LLP

(57) ABSTRACT

A structure used for animal cells is provided which includes an elastic body layer having a flat surface on which animal cells are left. The elastic body layer has a surface whose elasticity is changed by partially supporting the elastic body layer from the rear side or by changing a thickness of the elastic body layer.

11 Claims, 8 Drawing Sheets

(56) References Cited

OTHER PUBLICATIONS

Mackay J L et al., entitled "A Genetic Strategy for the Dynamic and Graded Control of Cell Mechanics, Motility, and Matrix Remodeling," Biophysical Journal, vol. 102, Feb. 2012, 434-442.
Jannat R A et al., entitled "Neutrophil adhesion and chemotaxis depend on substrate mechanics," J Phys Condesn Matter, May 19, 2010; 22(19): 194117, 22 pages.
Peyton S R et al., entitled "Extracellular Matrix Rigidity Governs Smooth Muscle Cell Motility in a Biphasic Fashion," Journal of Cellular Physiology 204:198-209 (2005).
Khatiwala C B et al., entitled "Intrinsic mechanical properties of the extracellular matrix affect the behavior of pre-osteoblastic MC3T3-E1 cells," Am J Physiool Cell Physiol 290:C1640-C1650, 2006.
Quinlan A M T et al., entitled "Investigating the role of substrate stiffness in the persistence of valvular interstitial cell activation," J Biomed Mater Res, Sep. 2012;100(9):2474-82.
Yeung T et al., entitled "Effects of Substrate Stiffness on Cell Morphology, Cytoskeletal Structure, and Adhesion," Cell Motility and the Cytoskeleton 60:24-34, 2005.
Paszek M J et al., entitled "Tensional homeostasis and the malignant phenotype," Cancer Cell, Sep. 2005, vol. 8, 241-254.
Du J et al., entitled "Integrin activation and internalization on soft ECM as a mechanism of induction of stem differentiation by ECM elasticity," PNAS, vol. 108, No. 23, Jun. 7, 2011, 9466-9471.
Treiser M D. et al., entitled "Cytoskeleton-based forecasting of stem cell lineage fates," PNAS, vol. 107, No. 2, Jan. 12, 2010, 610-615.
Kloxin A M et al., entitled "In situ elasticity modulation with dynamic substrates to direct cell phenotype," Biomaterials 31 (2010) 1-8.
Gilbert P M et al., entitled "Substrate Elasticity Regulates Skeletal Muscle Stem Cell Self-Renewal in Culture," Science, 329, 1078-1081, 2010.
Teixeira A I et al., entitled "The promotion of neuronal maturation on soft substrates," Biomaterials 30 (2009) 4567-4572.
Engler A J et al., entitled "Matrix Elasticity Directs Stem Cell Lineage Specification," Cell 126, 677-689, Aug. 25, 2006.
Kidoaki S entitled, "Elastic interface to manipulate cell functions: Bishiteki Zairyo Rikigaku Ryoshiba Sekkei ni yoru Saibo Kino Seigyo", Journal of Japanese Society for Biomaterials, 2009, vol. 27, No. 3, pp. 136-144.
Kidoaki S et al., entitled "Mechanotaxis: Seibutsu Kihan Saibo Sosa Zairyo no Sekkei", CSJ: The Chemical Society of Japan Dai 91 Shunki Nenkai (2011) Koen Yokoshu I, 2011, p. 38, 3H2-25.
Utsumi A, et al., entitled "Efficient manipulation of cell mechanotaxis: effect of the curvature of micro-elasticity boundary", Biophysics, 2012, vol. 52, Supp. 1, S108, 1PT232.
Isenberg B C, et al., entitled "Vascular smooth muscle cell durotaxis depends on substrate stiffness gradient strength", Biophys. J., 2009, vol. 97, No. 5, pp. 1313-1322.
Style R W, et al., entitled "Patterning droplets with durotaxis", Proc. Natl. Acad. Sci.USA, Jul. 2013, vol. 110, No. 31, pp. 12541-12544.
Choi Y S et al., entitled "The alignment and fusion assembly of adipose-derived stem cells on mechanically patterned matrices," Biomaterials, 2012, vol. 33, No. 29, p. 6943-6951.
PCT International Search Report dated Mar. 3, 2015 in connection with PCT International Patent Application No. PCT/JP2014/083247, 4 pages.
PCT International Preliminary Examination Report dated Feb. 9, 2016 in connection with PCT International Patent Application No. PCT/JP2014/083247, 15 pages.

* cited by examiner

STRUCTURE USED FOR ANIMAL CELLS, METHOD OF SEPARATING ANIMAL CELLS, AND METHOD OF ADJUSTING ELASTICITY OF SURFACE OF STRUCTURE USED FOR ANIMAL CELLS

TECHNICAL FIELD

The present invention relates to a structure used for animal cell, a method of separating animal cells, and a method of adjusting elasticity of a surface of a structure used for animal cells, wherein a three-dimensional shape having protrusions and recesses is used, and they are appropriate for controlling migration, proliferation and differentiation of animal cells in the fields of medical materials, medical devices, artificial organs, regenerative medicine, cell therapies, regenerative medical engineering, malignant neoplasm diagnosis, cell separation, and pathological diagnosis.

Priority is claimed on Japanese Patent Application No. 2013-261677, filed Dec. 18, 2013, the content of which is incorporated herein by reference.

BACKGROUND ART

Recently, a technology for adjusting elasticity of a soft material such as a structure for animal cell has been focused on. As the technology for adjusting elasticity of a soft material, the prior art described below is known.

(1) Technologies for adjusting elasticity using temperature control, such as a method in which elasticity of rubber is arbitrarily changed due to temperature (for example, refer to Patent Document 1) and a method in which elasticity of a separation membrane is adjusted by heat (for example, refer to Patent Document 2).

(2) Technologies for adjusting elasticity using a crosslinking density or a crosslinking method, such as a method in which a body formed using a collagen, a proteoglycan and a hyaluronic acid is subjected to thermal dehydration crosslinking, and thus elastic modulus of a predetermined level or higher thereof is maintained (for example, refer to Patent Document 3), a method in which a collagen gel having high elasticity used as a scaffold material is obtained by crosslinking using a chemical method or a physical method (for example, refer to Patent Document 4), a method in which crosslinking conditions of a collagen are changed, and thus elastic modulus of a collagen gel used as a cell lead-out substrate is adjusted (for example, refer to Patent Document 5), and a method in which a crosslinking (photocrosslinking) density of a hyaluronic acid gel is changed to adjust elastic modulusi of the hyaluronic acid gel (for example, refer to Patent Document 6).

(3) Technologies for adjusting elasticity by adding and dispersing an inorganic material, such as a method in which a clay mineral is dispersed in an acrylamide-based monomer to adjust elastic modulus of a polymer hydrogel which is obtained after polymerization thereof (for example, refer to Patent Document 7).

(4) Technologies for adjusting elasticity by performing a three-dimensional structure control, such as a method in which a collagen is porosified and thus elasticity is adjusted (for example, refer to Patent Document 8).

In addition, cells are known to have a tendency to migrate from a surface having a low elastic modulus to a surface having a high elastic modulus (for example, refer to Non-Patent Documents 1 to 8). As the prior art in which elasticity of a surface of a structure used for animal cell is selectively adjusted, a method in which an area in which a concentration of a crosslinking agent is different is arranged when a structure used for animal cell is manufactured (for example, refer to Non-Patent Documents 1 to 7) and a method using local photocrosslinking (for example, refer to Non-Patent Document 8) are known.

Furthermore, a technology for controlling a migration speed of cells (for example, refer to Non-Patent Documents 1, and 9 to 13), a technology for controlling a proliferation rate of cells (for example, refer to Non-Patent Document 14), a technology in which a morphological change of cells resulting from a change in elastic modulus of a surface is used (refer to Non-Patent Documents 2, 9, and 14 to 16), and a technology in which a change in a degree of differentiation and a change in a differentiation direction of cells resulting from a difference of elastic modulus of a surface are used (refer to Non-Patent Documents 17 to 22) are known.

CONVENTIONAL ART DOCUMENTS PATENT DOCUMENTS

Patent Document 1:
  Japanese Unexamined Patent Application, First Publication No. 2001-65617
Patent Document 2:
  Japanese Unexamined Patent Application, First Publication No. H11-347382
Patent Document 3:
  Japanese Unexamined Patent Application, First Publication No. 2013-150648
Patent Document 4:
  Japanese Unexamined Patent Application, First Publication No. 2012-130386
Patent Document 5:
  Japanese Unexamined Patent Application, First Publication No. 2012-126681
Patent Document 6:
  Published Japanese Translation No. H11-512778 of the PCT International Publication
Patent Document 7:
  Japanese Unexamined Patent Application, First Publication No. 2005-232402
Patent Document 8:
  Japanese Unexamined Patent Application, First Publication No. 2011-225462

NON-PATENT DOCUMENTS

Non-Patent Document 1:
  C. M. Lo, H. B. Wang, M. Dembo and Y. L. Wang, Biophys J, 2000, 79, 144-152.
Non-Patent Document 2:
  G. Jiang, A. H. Huang, Y. Cai, M. Tanase and M. P. Sheetz, Biophys J, 2006, 90, 1804-1809.
Non-Patent Document 3:
  A. Welle, A. Chiumiento and R. Barbucci, Biomol Eng, 2007, 24, 87-91.
Non-Patent Document 4:
  K. A. Lazopoulos and D. Stamenovic, J Biomech, 2008, 41, 1289-1294.
Non-Patent Document 5:
  P. C. Fung, Chin Med, 2009, 4, 10.
Non-Patent Document 6:
  B. C. Isenberg, P. A. Dimilla, M. Walker, S. Kim and J. Y. Wong, Biophys J, 2009, 97, 1313-1322.
Non-Patent Document 7:
  B. Harland, S. Walcott and S. X. Sun, Phys Biol, 2011, 8, 015011.

Non-Patent Document 8:
T. Kawano and S. Kidoaki, Biomaterials, 2011, 32, 2725-2733.
Non-Patent Document 9:
B. Ananthanarayanan, Y. Kim and S. Kumar, Biomaterials, 2011, 32, 7913-7923.
Non-Patent Document 10:
J. L. MacKay, A. J. Keung and S. Kumar, Biophys J, 2012, 102, 434-442.
Non-Patent Document 11:
R. A. Jannat, G. P. Robbins, B. G. Ricart, M. Dembo and D. A. Hammer, J Phys Condens Matter, 2010, 22, 194117.
Non-Patent Document 12:
S. R. Peyton and A. J. Putnam, J Cell Physiol, 2005, 204, 198-209.
Non-Patent Document 13:
C. B. Khatiwala, S. R. Peyton and A. J. Putnam, Am J Physiol Cell Physiol, 2006, 290, C1640-1650.
Non-Patent Document 14:
A. M. Quinlan and K. L. Billiar, J Biomed Mater Res A, 2012, 100, 2474-2482.
Non-Patent Document 15:
T. Yeung, P. C. Georges, L. A. Flanagan, B. Marg, M. Ortiz, M. Funaki, N. Zahir, W. Ming, V. Weaver and P. A. Janmey, Cell Motil Cytoskeleton, 2005, 60, 24-34.
Non-Patent Document 16:
M. J. Paszek, N. Zahir, K. R. Johnson, J. N. Lakins, G. I. Rozenberg, A. Gefen, C. A. Reinhart-King, S. S. Margulies, M. Dembo, D. Boettiger, D. A. Hammer and V. M. Weaver, Cancer Cell, 2005, 8, 241-254.
Non-Patent Document 17:
J. Du, X. Chen, X. Liang, G. Zhang, J. Xu, L. He, Q. Zhan, X. Q. Feng, S. Chien and C. Yang, Proc Natl Acad Sci USA, 2011, 108, 9466-9471.
Non-Patent Document 18:
M. D. Treiser, E. H. Yang, S. Gordonov, D. M. Cohen, I. P. Androulakis, J. Kohn, C. S. Chen and P. V. Moghe, Proc Natl Acad Sci USA, 2010, 107, 610-615.
Non-Patent Document 19:
A. M. Kloxin, J. A. Benton and K. S. Anseth, Biomaterials, 2010, 31, 1-8.
Non-Patent Document 20:
P. M. Gilbert, K. L. Havenstrite, K. E. Magnusson, A. Sacco, N. A. Leonardi, P. Kraft, N. K. Nguyen, S. Thrun, M. P. Lutolf and H. M. Blau, Science, 2010, 329, 1078-1081.
Non-Patent Document 21:
A. I. Teixeira, S. Ilkhanizadeh, J. A. Wigenius, J. K. Duckworth, O. Inganas and O. Hermanson, Biomaterials, 2009, 30, 4567-4572.
Non-Patent Document 22:
A. J. Engler, S. Sen, H. L. Sweeney and D. E. Discher, Cell, 2006, 126, 677-689.

DISCLOSURE OF INVENTION

Problem to be Solved by the Invention

However, the method using temperature control, the various crosslinking methods, and the method in which elasticity of an elastic body is adjusted by adding and dispersing an inorganic material or the like described in Patent Documents 1 to 8 are methods that can be applied to only an elastic body to which heating, crosslinking, or addition and dispersion of an inorganic material can be applied, and therefore they are not applicable to all elastic bodies. In addition, for example, when a crosslinking density of an elastic body is differently set, it is possible to change elastic modulus of a surface of the elastic body. However, properties other than elasticity of the surface of the elastic body may be changed according to a change of the crosslinking density. That is, there are risks of properties of the surface other than elasticity, for example, hydrophilicity, hydrophobicity, charge, roughness and the like being changed, and compatibility as a structure for animal cell such as a soft material may be decreased (problem point 1).

In addition, in the method in which a crosslinking density and a crosslinking structure are locally changed to adjust elasticity of a surface of an elastic body, since a change in a volume is caused by crosslinking, flatness of the surface may be lost. Currently, as a method in which a crosslinking density is locally changed in a surface of an elastic body of a structure used for animal cell, a method through which the finest formation is possible is a photocrosslinking method. However, in this case, flatness is also lost, and a resolution is only about several μm to several tens of μm. In addition, in such methods, it is difficult to set a resolution to be smaller than 1 μm due to a problem of a diffraction limit of light. In addition, an application to an elastic body through which light is unable to pass is difficult (problem point 2).

In addition, various types of cells coexist in biological tissues. In order to artificially manipulate a coexistence state of such cells in a living body, various structures for animal cell are manufactured. As can be seen in Non-Patent Documents 1 to 22 described above, it is known that, when elasticity of a surface of the structure for animal cell is adjusted, migration, proliferation, differentiation and metabolism of animal cells can be controlled. When elasticity is locally adjusted, a possibility of collecting cells in a desired form may be feasible.

However, in the present circumstances, adjustment of elasticity of a surface of the structure used for animal cell is limited only to a material wherein crosslinking is possible. In addition, even when the photocrosslinking method is used, since a resolution obtained by the method is only about several μm to several tens of μm, collecting cells in a desired form has not been accomplished (problem point 3).

The present invention has been made in view of the above-described circumstances, and an object of the present invention is to provide a structure used for animal cells, a method of separating animal cells, and a method of adjusting elasticity of a surface of a structure used for animal cells through which it is possible to address the problem points 1 to 3 described above.

Furthermore, since migration, proliferation and differentiation functions of animal cells are also influenced by roughness of a nanometer scale, an influence of a minute change in a shape of a surface resulting from crosslinking on such functions of animal cells should be considered. In consideration of easy control of functions of cells according to adjustment of elasticity, it is preferable that a surface of a scaffold material be flat. Accordingly, an object of the present invention is to provide a method of adjusting elasticity of a surface of any structure used for animal cells through which it is possible to adjust elasticity of the surface thereof with a high resolution (about 1 μm) without changing the surface shape of the structure used for animal cells, and it is possible to collect cells in a desired form.

That is, an object of the present invention is to provide a structure used for animal cells, a method of separating animal cells, and a method of adjusting elasticity of a surface of a structure used for animal cells, that are appropriate for controlling migration, proliferation and differentiation of animal cells, can be applied to any elastic body, use a three-dimensional shape through which fine adjustment of elasticity is possible in a simple manner with a high resolution, and can be performed without a change in properties other than elasticity, for example, flatness, and without a change in shape.

Means for Solving the Problem

The inventors have conducted extensive studies to address the problem points 1 to 3 described above and found that, when elasticity of a surface of an elastic body layer of a structure used for animal cells is changed by partially supporting the elastic body layer from the rear side or by changing a thickness of the elastic body layer, the invention can be applied to any elastic body and can be manufactured in a simple manner without changing properties of the surface other than elasticity, and completed the present invention.

Specifically, the inventors found that, by changing elasticity of the surface of the elastic body layer described above, it is possible to easily adjust elasticity of the surface of the elastic body layer, flatness of the surface is not lost even when elasticity is changed, and it is possible to adjust elasticity with a high resolution (about 1 μm).

In addition, the inventors found that, when elasticity of the surface of the elastic body is changed according to the substrate layer that supports the elastic body layer from the rear side or by a three-dimensional shape of the elastic body layer, since elasticity of a surface of any structure used for animal cell can be adjusted with a high resolution (about 1 μm), migration, proliferation and differentiation of animal cells on the surface of the structure used for animal cells obtained in this manner are accurately controlled.

That is, the present invention relates to a structure used for animal cells, a method of separating animal cells, and a method of adjusting elasticity of a surface of a structure used for animal cells described below, wherein a three-dimensional shape which is appropriate for controlling migration, proliferation and differentiation of animal cells is used.

(1) A structure used for animal cells including: an elastic body layer having a flat surface on which animal cells are provided, wherein the elasticity of the flat surface of the elastic body layer is changed by partially supporting the elastic body layer from the rear side or by changing a thickness of the elastic body layer.

(2) The structure used for animal cells according to item (1), further including a substrate layer that partially supports the elastic body layer from the rear side, wherein the substrate layer has a three-dimensional shape having protrusions and recesses which includes a first substrate layer that supports the elastic body layer and a second substrate layer that does not support the elastic body layer, and wherein the elasticity of the surface of the elastic body layer is changed according to the uneven three-dimensional shape.

(3) The structure used for animal cells according to item (1), wherein the rear side of the elastic body layer is formed in a three-dimensional shape having protrusions and recesses and a thickness of the elastic body layer is changed according to the uneven three-dimensional shape.

(4) The structure used for animal cells according to item (3), further including a substrate layer that supports the elastic body layer from the rear side.

(5) The structure used for animal cells according to item (4), wherein the substrate layer is formed in a three-dimensional shape having protrusions and recesses corresponding to the three-dimensional shape of the elastic body layer and supports the entire elastic body layer.

(6) The structure used for animal cells according to any of items (1) to (5), wherein the substrate is a substrate which controls migration, proliferation and differentiation of animal cells.

(7) A method of separating animal cells using the structure used for animal cells according to any of items (1) to (6).

(8) A method of adjusting the elasticity of a surface of a structure used for animal cells, wherein the method uses the structure used for animal cells according to any of items (1) to (6).

Effects of Invention

In a structure used for animal cells and a method of adjusting elasticity of a surface of a structure used for animal cells of the present invention, elasticity of the surface of the structure used for animal cells can be changed according to a substrate layer or a three-dimensional shape of the elastic body layer. Therefore, the invention can be applied to any elastic body, properties of the surface other than elasticity are not changed even when elasticity of the elastic body layer is changed, and the method of adjusting elasticity can be implemented in a simple manner. Therefore, the problem point 1 can be solved by the invention.

Control of migration, proliferation and differentiation of animal cells on the elastic body of the present invention can be achieved by changing elasticity of the surface of the structure used for animal cells according to the three-dimensional shape of the substrate layer or the elastic body layer. That is, due to an unevenness of the substrate layer or an unevenness of the elastic body layer, elasticity of the surface of the elastic body layer is not continuously changed from a part that is supported by the substrate to a part that is not supported by the substrate, but elasticity of the surface is suddenly changed so that a boundary becomes clear, and a difference of elastic modulus can be exactly adjusted. For this reason, elasticity of the surface of any structure used for animal cells can be adjusted with a high resolution (about 1 μm), and an application to an elastic body through which light is unable to pass is possible. Therefore, the problem point 2 can be addressed.

In the structure used for animal cells of the present invention, crosslinking is unnecessary, and it is possible to adjust elasticity of a surface with a high resolution (about 1 μm) and it is possible to collect and separate animal cells in a desired form, without changing a shape of the surface of any structure used for animal cells. Therefore, the problem point 3 can be addressed. That is, cell tissues having the desired shape (for example, a quadrangular cell sheet) can be obtained, for example, when a shape of a (hard) part having a high elastic modulus of the surface is set to a desired shape to form a cell cluster (a cell aggregation), for example, a quadrangle.

BEST MODE FOR CARRYING OUT THE INVENTION

Forms for implementing a structure used for animal cells and a method of adjusting elasticity of a surface of a structure used for animal cells according to the present invention will be described below, wherein a three-dimensional shape having protrusions and recesses which is appropriate for controlling migration, proliferation and differentiation of animal cells is used. Hereinafter, while methods and use examples of the present invention will be described in detail based on embodiments for implementing the present invention, the present invention is not limited to such embodiments.

A structure used for animal cells using a three-dimensional shape having protrusions and recesses of an elastic body layer or a substrate layer and a method of adjusting elasticity of a surface of the structure used for animal cells according to the present invention will be described with reference to the drawings.

Figure 1A:
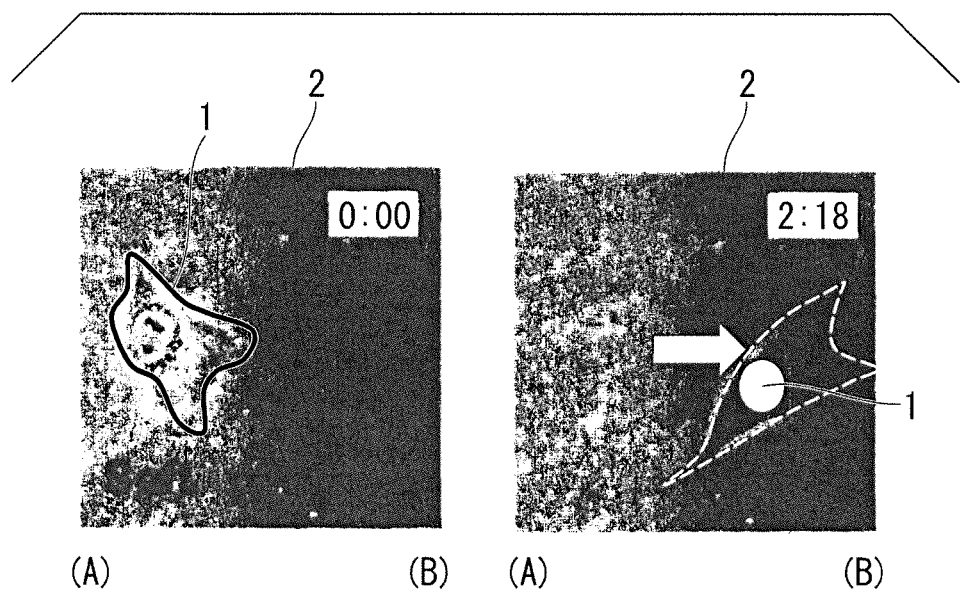
FIG. 1A is a photographic view showing durotaxis of an animal cell.
Figure 1B:
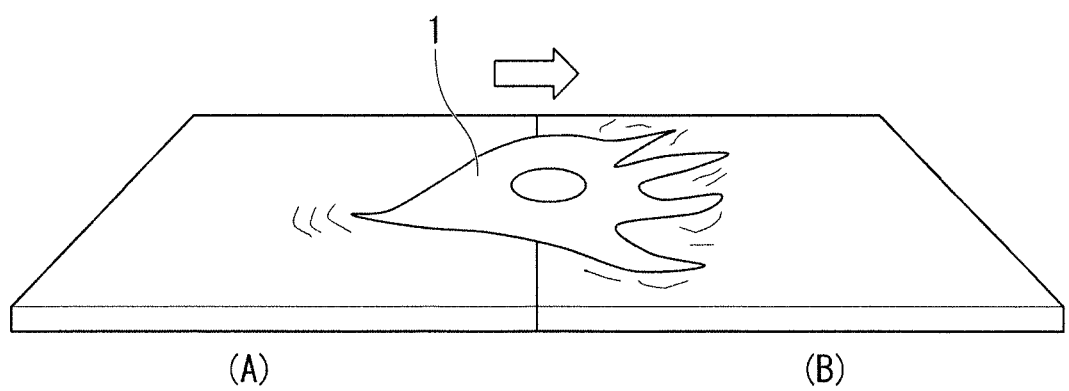
FIG. 1B is a schematic diagram illustrating durotaxis of an animal cell.

Elasticity of a structure used for animal cells is being actively discussed in the fields of regenerative medical engineering in addition to cell biology and biophysics since it was found that animal cells have a characteristic of "durotaxis" in which cells preferentially migrate from a soft to a hard surface (Lo et al., Biophys. J., 2000). FIG. 1A is a photographic view shown in the above document and shows an animal cell 1 left on an elastic body layer 2 that has moved from a soft area surface (A) to a hard area surface (B) with the passage of time from the left to the right. Therefore, since animal cells have a characteristic of "durotaxis" in which cells preferentially migrate to a hard surface, as illustrated in FIG. 1B, the animal cell 1 can be called as a micro sensor which can recognize "a difference of elastic modulus." (FIG. 1B). It has been reported that "a difference of elastic modulus" adjusts not only adherence, movement, and proliferation of cells but also differentiation (for example, Engler et al., Cell, 2006, Gilbert et al., SCIENCE, 2010).

The structure used for animal cells of the present invention includes an elastic body layer having a flat surface on which animal cells are provided. In the elastic body layer, elasticity of the surface is changed by partially supporting the elastic body layer from the rear side or by changing a thickness of the elastic body layer.

Hereinafter, an embodiment in which elasticity of the surface is changed by partially supporting the elastic body layer from the rear side is referred to as a "first form," and an embodiment in which elasticity of the surface is changed according to a change in a thickness of the elastic body layer is referred to as a "second form."

(First Form)

In the first form of the present invention, elasticity of a surface of an elastic body layer is changed by partially supporting the elastic body layer from the rear side.

When the elastic body layer has elasticity, stiffness of a surface thereof may be changed according to whether it is supported from a lower surface (a rear surface). That is, by being supported from the rear surface, the supported surface has a relatively high modulus of elasticity and becomes relatively hard. In view of such a phenomenon, by changing whether it is supported from the rear surface, it is possible to change elasticity of the surface on which animal cells are left.

Figure 8A:
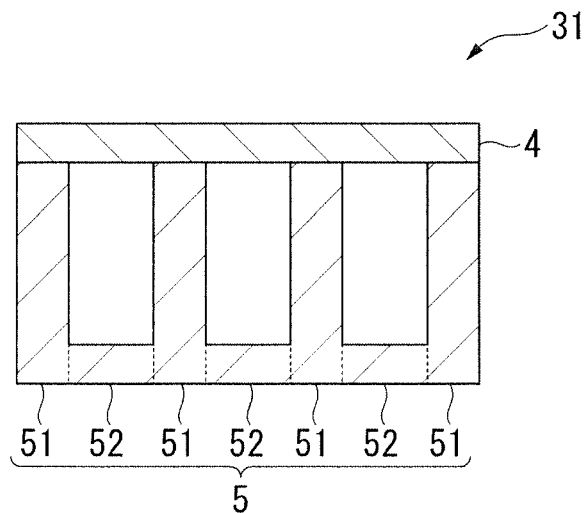
FIG. 8A is a schematic diagram illustrating an example of a structure used for animal cells of the present invention.

FIG. 8A illustrates a further detailed configuration of a structure used for animal cells 31 according to the first form of the present invention. The structure used for animal cells 31 includes an elastic body layer 4 and a substrate layer 5 that partially supports the elastic body layer 4 from the rear side. The substrate layer 5 includes a first substrate layer portion 51 that supports the elastic body layer 4 and a second substrate layer portion 52 that does not support the elastic body layer 4 and has a three-dimensional shape having protrusions and recesses. Elasticity of a surface of the elastic body layer 4 can be changed according to the three-dimensional shape. Also, in FIG. 8A, while the first substrate layer portion 51 and the second substrate layer portion 52 are separately described, it is preferable that the first substrate layer portion 51 and the second substrate layer portion 52 be integrally formed in the same member.

(Second Form)

In the second form of the present invention, elasticity of a surface of an elastic body layer is changed according to a change in a thickness of the elastic body layer.

When the elastic body layer has elasticity, stiffness of the surface may be easily changed when a thickness of the elastic body layer itself is changed. That is, when a three-dimensional shape having protrusions and recesses is formed in the elastic body layer, elastic modulus of the surface is relatively low on a valley portion having a small thickness, and elastic modulus of the surface is relatively high on a peak portion having a large thickness. In addition, when a three-dimensional shape having protrusions and recesses is formed on a rear surface, it is possible to change elasticity of the surface on which animal cells are provided even if the surface itself is flat.

Figure 8B:
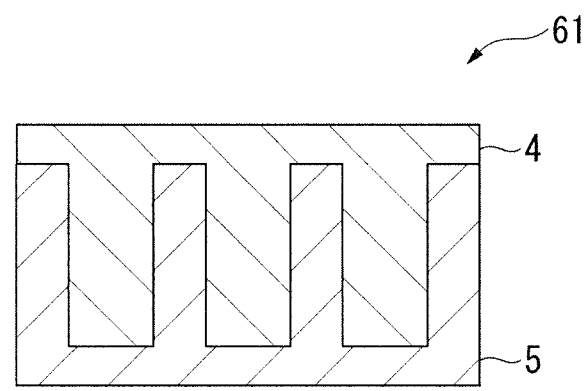
FIG. 8B is a schematic diagram illustrating an example of a structure used for animal cells of the present invention.
Figure 8C:
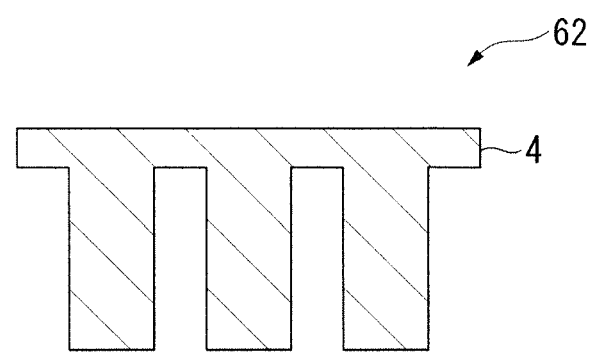
FIG. 8C is a schematic diagram illustrating an example of a structure used for animal cells of the present invention.

FIGS. 8B to 8C illustrate a further detailed configuration of structures used for animal cells 61 and 62 according to the second form of the present invention. In the structures 61 and 62, the rear side of the elastic body layer 4 has a three-dimensional shape having protrusions and recesses, and a thickness of the elastic body layer 4 is changed according to the three-dimensional shape. Accordingly, it is possible to change elasticity of a surface of the elastic body layer 4.

As illustrated in FIG. 8B, the elastic body layer 4 of the structure used for animal cells 61 may be supported by the substrate layer 5 from the rear side. As illustrated in FIG. 8C, the elastic body layer 4 of the structure used for animal cells 62 may not be supported by the substrate layer 5 or the like.

In addition, when the structures 61 and 62 of the second form are supported by the substrate layer 5, the substrate layer 5 having a three-dimensional shape having protrusions and recesses corresponding to the three-dimensional shape formed on a rear surface of the elastic body layer 4 is used, the entire elastic body layer 4 (the entire rear surface) may be supported by the substrate layer 5 (FIG. 8B), or only a part of the elastic body layer 4 may be supported by the substrate layer 5 (not illustrated). As an example of the latter, the single elastic body layer 4 illustrated in FIG. 8C (placed on a flat substrate) supported by the flat substrate layer 5 (for example, a glass substrate) may be exemplified.

Hereinafter, more specifically, the present invention will be described with reference to embodiments.

Embodiment 1

Figure 2A:
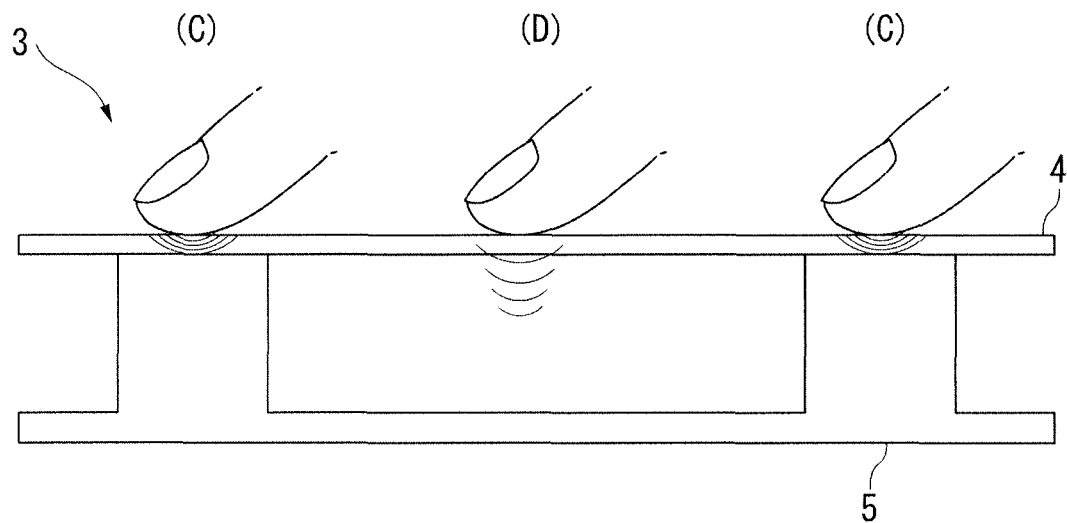
FIG. 2A is a schematic diagram illustrating a principle of adjustment of elasticity in Embodiment 1.

The present invention relates to a structure used for animal cells, a method of separating animal cells, and a method of adjusting elastic modulus of a surface of the structure used for animal cells through which it is possible to exactly adjust "a difference of elastic modulus." In Embodiment 1 of the present invention, as illustrated in FIG. 2A, a structure used for animal cells 3 includes the elastic body layer 4 and the substrate layer 5. Embodiment 1 corresponds to the first form.

The elastic body layer 4 is made of a synthetic resin and/or a natural fiber, or a thin film or a fiber prepared using the same. Also, the elastic body layer 4 includes an elastic body layer portion (C) that is supported by the substrate layer 5 and an elastic body layer portion (D) that is not supported by the substrate layer 5. A three-dimensional shape having protrusions and recesses of the substrate layer 5 is formed by a substrate layer portion that supports the elastic body layer portion (C) and a substrate layer portion that does not support the elastic body layer portion (D). Accordingly, the elastic body layer portion (C) that is supported by the substrate layer 5 becomes a hard surface whose modulus of elasticity is locally high, and the elastic body layer portion (D) that is not supported by the substrate layer 5 becomes a soft surface whose modulus of elasticity is low.

Figure 2B:
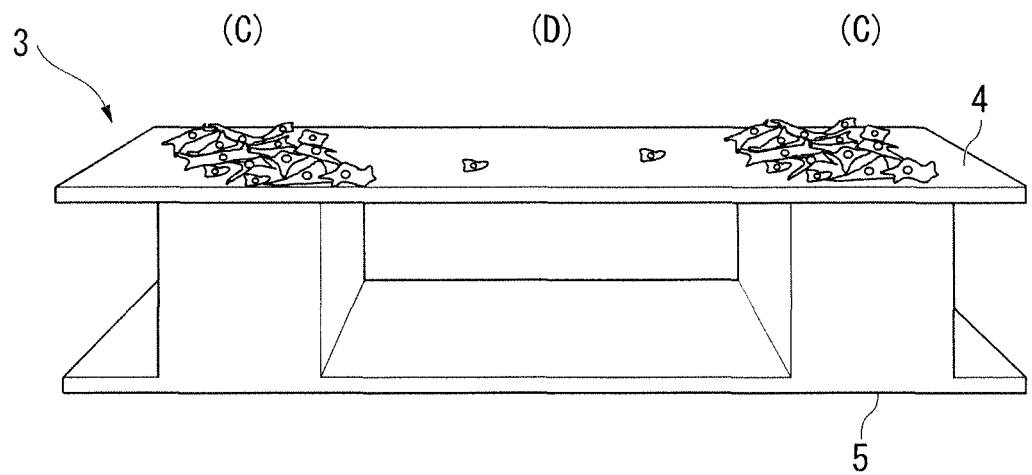
FIG. 2B is a schematic diagram illustrating a concept of a use example of a structure used for animal cells in Embodiment 1.

FIG. 2B is a conceptual diagram illustrating that a large amount of the animal cells 1 are aggregated on the elastic body layer portion (C) that is supported by the substrate layer 5 when animal cells are cultured on the structure used for animal cells 3 which is formed according to Embodiment 1 of the present invention.

Embodiment 2

Figure 3A:
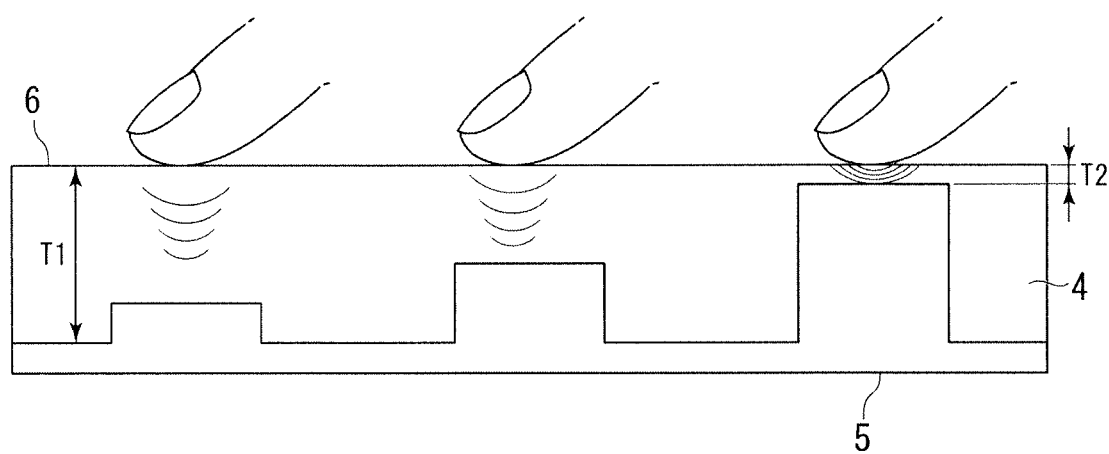
FIG. 3A is a diagram illustrating a principle of adjustment of elasticity of an elastic body in Embodiment 2.

As a structure used for animal cells, a method of classifying animal cells, and a method of adjusting elastic modulus of a surface of the structure used for animal cells through which the "difference of elastic modulus" can be exactly adjusted, Embodiment 2 of the present invention is shown in FIG. 3A. Embodiment 2 corresponds to the second form.

As illustrated in FIG. 3A, similarly to Embodiment 1, in Embodiment 2 of the present invention, the structure used for animal cells 6 includes the elastic body layer 4 and the substrate layer 5. In Embodiment 2 of the present invention, the elastic body layer 4 is supported by the substrate layer 5. By changing a thickness of the elastic body layer 4 according to a three-dimensional shape having protrusions and recesses of a surface of the substrate layer 5, a three-dimensional shape having protrusions and recesses is formed on a rear surface of the elastic body layer 4. Accordingly, in a surface of the structure used for animal cells 6, a thin part of the elastic body layer 4 becomes a hard surface whose modulus of elasticity is locally high, and a thick part of the elastic body layer 4 becomes a soft surface whose modulus of elasticity is low.

Figure 3B:
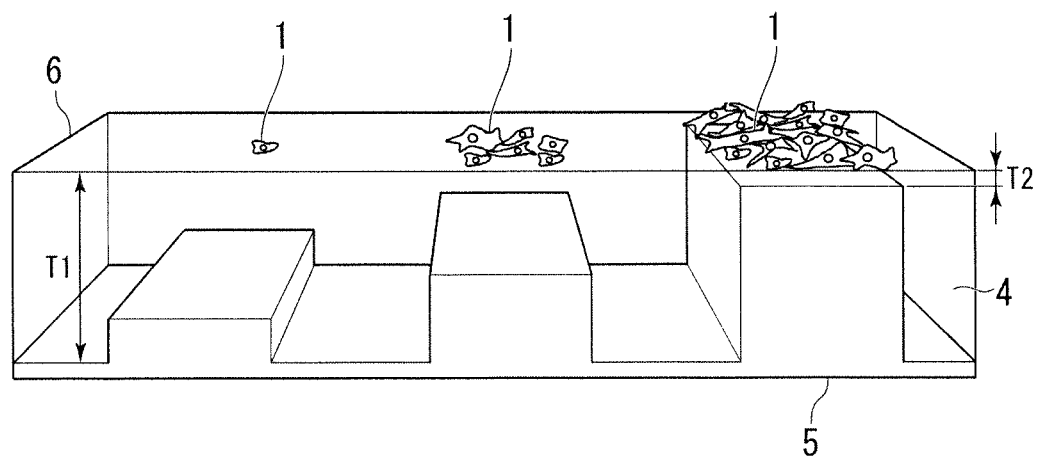
FIG. 3B is a diagram illustrating a use example of a structure used for animal cells in Embodiment 2.

FIG. 3B is a conceptual diagram illustrating that a large amount of the animal cells 1 are aggregated on the thin part of the elastic body layer 4 when animal cells are cultured on the structure used for animal cells 6 formed according to Embodiment 2 of the present invention.

In addition, FIG. 3B illustrates that, by gradually changing a thickness of the elastic body layer 4, the number of aggregated animal cells and types of cells can be different accordingly.

As described above, in the structure used for animal cells 3 and 6, by the elastic body layer portion (C) that is supported by the substrate layer 5 and the elastic body layer portion (D) that is not supported by the substrate layer 5, and by changing a thickness of the elastic body layer 4 according to the three-dimensional shape of the substrate layer 5 as necessary to form a three-dimensional shape having protrusions and recesses on the rear surface of the elastic body layer 4, it is possible to form a hard surface whose elastic modulus is locally high on the surface of the structures used for animal cells 3 and 6 by locally changing a part of the elastic body layer 4 that is supported.

That is, according to the present invention, only by changing a thickness of the elastic body layer 4 and/or by locally changing whether it is supported by the substrate layer 5, it is possible to change the elastic modulus of the surface of the structures 3 and 6.

Exemplary methods of manufacturing a structure used for animal cells of the present invention include: a manufacturing method in which an unevenness is formed on a surface of a substrate by etching or the like and an elastic sheet of an elastic body layer is placed thereon (for example, the structure 31 of the first form); a manufacturing method in which an elastic material is applied to a substrate after an unevenness is formed on the surface of the substrate similarly to the above, and a top surface of a peak portion and a valley portion of the unevenness is embedded using the elastic material (for example, the structure 61 of the second form); and a manufacturing method in which a lower part of an elastic body layer is formed with an unevenness and placed on a flat substrate as necessary (for example, the structure 62 of the second form). In addition, the method of forming an unevenness in a lower part of the elastic body layer is not particularly limited. For example, similarly to the above, an elastic material is applied to the substrate after an unevenness is formed on the surface thereof, a top surface of a peak portion and a valley portion of the unevenness is embedded by the elastic material, and the elastic material is dried. Then, by peeling off only the elastic material (the elastic body layer) from the substrate, it is possible to obtain the elastic body layer having an unevenness on a rear surface (a lower part).

The elastic material which forms the elastic body layer is not particularly limited. Any material having elasticity such as a polymer material and a rubber material can be used. In addition, a rigid material such as glass, a silicon, a plastic, and a metal, and a flexible material having higher hardness than the elastic body layer can be used as a substrate of the substrate layer.

Next, an embodiment in which a structure used for animal cells of the present invention is manufactured will be described.

The structure used for animal cells of the present embodiment is manufactured by adhering a thin film of an elastic body layer onto a substrate layer formed in a three-dimensional shape having protrusions and recesses.

First, a method of manufacturing a thin film of an elastic body layer will be described below. An aqueous solution of a polyvinyl alcohol (hereinafter, referred to as "PVA") at a concentration of 70.6 g/l was fully spin-coated (4000 rpm, 50 sec) on a round cover glass from which dust has been sufficiently away due to blow of nitrogen gas ($N_2$). Next, on the round cover glass coated with the PVA, a chloroform solution of a polycaprolactone (hereinafter, referred to as "PCL") of 13.7 g/l was applied to cover about 80 to 90% of an area of the round cover glass and spin coating was performed (4000 rpm, 50 sec). Accordingly, a PCL film having a uniform thickness (about 50 μm) was formed on the round cover glass.

Furthermore, a method in which an elastic body thin film is adhered to a substrate having a three-dimensional shape having protrusions and recesses will be described in detail below.

First, a substrate having a three-dimensional pattern having protrusions and recesses of a 1 cm square was adhered and fixed to a center of a new round cover glass by manicure. Then, using a sponge swab and a Pasteur pipette, Vaseline (registered trademark) was applied to the surroundings of the substrate in a circular shape and the Vaseline (registered trademark) was radially dispersed outward therefrom. EUKITT (product name, commercially available from O Kindler GmbH & Co, Germany, encapsulant) was dropped at an appropriate amount to an interval between the radial Vaseline (registered trademark). Before the EUKITT was dried, a cover glass on which the PCL film was formed was adhered to the substrate such that the PCL film surface faces downward. In order to increase adhesiveness, a weight was placed directly above the pattern substrate and left overnight. According to the above procedures, the substrate having a three-dimensional pattern having protrusions and recesses was interposed between two sheets of cover glass. Then, after the EUKITT was dried, the substrate having a three-dimensional pattern having protrusions and recesses interposed between two sheets of cover glass, which were under preparation, was input to a 100 mm dish, immersed in degassed water overnight. According to dissolution of the PVA, one sheet of cover glass was peeling off, and only the PCL film remained on the substrate having a three-dimensional pattern having protrusions and recesses. After the cover glass was removed, water inside the dish was discharged, moisture was lightly removed with KimWipes and then drying was performed. Next, VECTA SHIELD (product name, commercially available from Vector Laboratories, Inc, encapsulant) was dropped at an appropriate amount to one side of a washer, and the washer was placed such that a center of a hole of the washer overlaps a center portion of the substrate. Further, in order to increase adhesiveness, a weight was placed on the washer and left overnight. According to the above procedures, the PCL film adhered to the three-dimensional pattern was protected by the washer, and adhesiveness and flatness increased. It was possible to adhere the PCL film to the substrate having a three-dimensional pattern having protrusions and recesses.

In the related art, since adjustment of elasticity was performed by a crosslinking method, a fine shape change may occur or a chemical characteristic may be changed due to crosslinking. It was very difficult to exactly adjust only elasticity in one polymer membrane. On the other hand, in the present invention, a three-dimensional shape having protrusions and recesses of the elastic body layer 4 or the substrate layer 5 is formed, and it is possible to change elastic modulus of the surface of the structures 3 and 6 only by changing a thickness of the elastic body layer 4 or by partially changing whether the elastic body layer 4 is supported by the substrate layer 5. Therefore, in the present invention, since a shape of the substrate layer 5 for support or non-support of the elastic body layer 4 or a thickness of the elastic body layer 4 is simply changed, crosslinking is unnecessary, and there is no need to choose a type of the elastic body layer 4. In addition, without changing a material of the elastic body layer 4, elasticity can be adjusted, and particularly, it is possible to exactly adjust elasticity with a resolution of a nano to several micrometer scale in the surface of the elastic body layer 4.

Other Embodiments

While the embodiments of the present invention have been described above, the present invention is not limited to the above embodiments, but can include various embodiments.

That is, since elastic modulus of the surface of the structure used for animal cells of the present invention is changed not only by elastic modulus of the elastic body layer itself, a thickness of the elastic body layer, and support or non-support of the elastic body layer by the substrate layer but also by a shape of a vertex part of the three-dimensional shape, adjustment is possible according to a combination of these factors.

In addition, by the three-dimensional shape, when a center surface of the elastic body layer has a higher modulus of elasticity and becomes harder than the other surface, animal cells can be collected at a center of the surface of the structure used for animal cells, or when a peripheral portion surface of the elastic body layer has a higher modulus of elasticity and becomes harder than the other surface, it is possible to collect animal cells at the peripheral portion surface of the structure used for animal cells. Therefore, it is possible to form a tissue cell sheet of a desired shape and separate animal cells to a desired part.

In addition, the three-dimensional shape having protrusions and recesses can have any pattern such as a radial pattern, a scaly pattern, a checkered pattern, and a honeycomb-like pattern in addition to a stripe pattern and a rectangular columnar pattern.

Furthermore, the vertex part of the three-dimensional shape can have a shape such as a triangular pyramid and a conical shape in addition to a planar shape.

EXAMPLES

Example 1

Similarly to the embodiment in which the structure used for animal cells was manufactured described above, a structure used for animal cells of the first form was manufactured.

Specifically, a film made of a synthetic polymer PCL that was frequently used as a biological material was attached to a substrate layer having a three-dimensional shape having protrusions and recesses of a stripe pattern as an elastic body layer, and the structure used for animal cells of the first form illustrated in a schematic diagram of FIG. 8A was obtained. It was possible to exactly adjust elasticity of a surface of this rectangular structure used for animal cell with a resolution of a nano to several micrometer scale.

Figure 4:
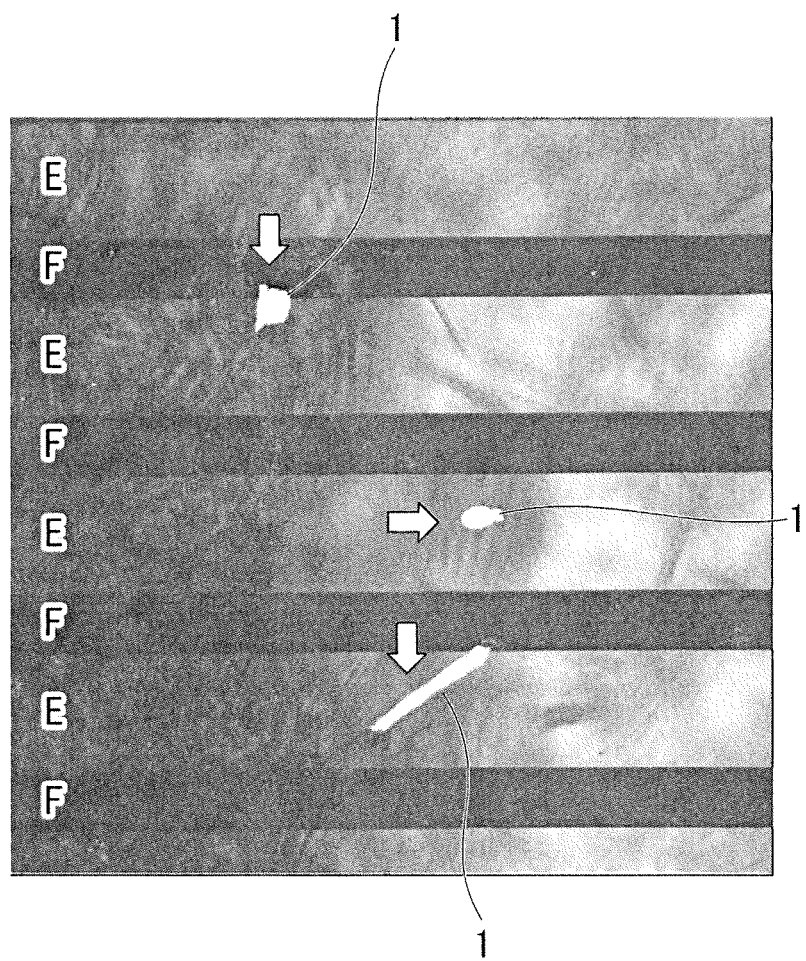
FIG. 4 is a diagram illustrating a localization of animal cells on a flat film (an elastic body layer) that is provided on a substrate layer having a stripe pattern in Example 1.

When NIH3T3 cells were cultured on the obtained structure used for animal cells, as illustrated in FIG. 4, it can be seen that the animal cells 1 were not aggregated at a part F which corresponds to valley portion of the substrate layer in which a polymer layer (a PCL film) serving as the elastic body layer was not supported by the substrate layer. On the other hand, the animal cells 1 were aggregated at a part in which the peak portion of the substrate layer was provided and a polymer layer (a PCL film) serving as the elastic body layer was in contact with the substrate layer, that is, a part E in which the elastic body layer was supported by the substrate layer.

Accordingly, it was confirmed that, only by locally changing support or non-support of the elastic body layer 4, it is possible to change elastic modulus of the surface of the structure used for animal cells 3 with a resolution of a nano to several micrometer scale, and migration or proliferation of the animal cells (the NIH3T3 cells) can be controlled using a change in the elasticity and a localization thereof can be controlled.

Example 2

The structure used for animal cells 3 in which a polymer membrane having a thickness of about 50 μm which forms the elastic body layer 4 having a flat surface was adhered to the substrate layer 5 in which a stripe groove 7 having a depth of 20 μm and a width of 25 μm was formed was obtained.

Figure 5A:
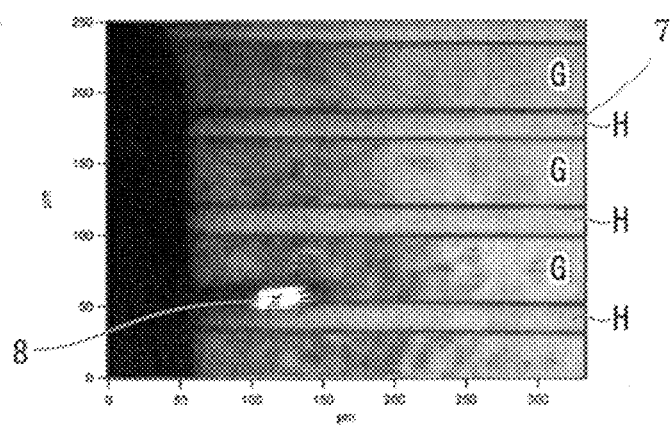
FIG. 5A shows an image obtained by measuring a shape image and a phase image on a polycaprolactone film provided on a substrate layer having a stripe pattern in an AFM resonance mode in Example 2.
Figure 5B:
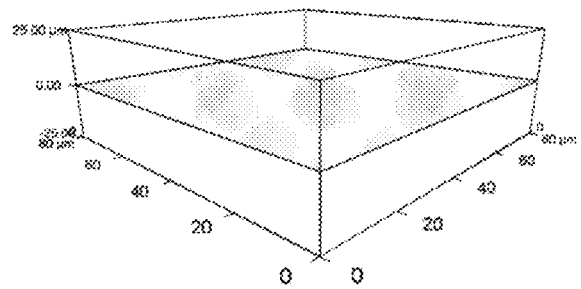
FIG. 5B is a diagram illustrating a shape image of a structure used for animal cells of Example 2 measured in the AFM resonance mode.
Figure 5C:
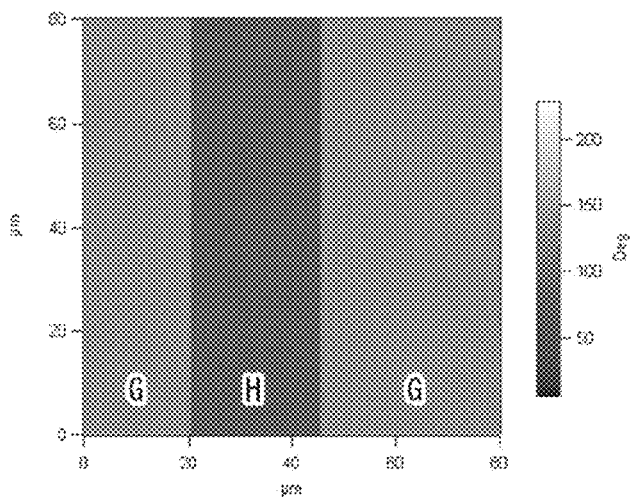
FIG. 5C is a diagram illustrating a phase image of the structure used for animal cells of Example 2 measured in the AFM resonance mode.

As shown in FIG. 5A, measurement was performed in a resonance mode of an atomic force microscope (AFM). FIGS. 5B and 5C are photographic views of a shape image and a phase image of a membrane surface of the structure used for animal cells 3 obtained in the AFM resonance mode. As shown in FIG. 5B, it can be seen that, regardless of the polymer membrane forming the elastic body layer 4 that was almost flat, the phase image of FIG. 5C had clear contrast. In addition, similarly to FIG. 4 of Example 1, it was confirmed that, when the animal cells 1 were cultured on the polymer membrane of the elastic body layer 4, the animal cells 1 were not aggregated at a part H in which a valley portion of the substrate layer 5 was provided, but aggregated at a part G in which a peak portion of the substrate layer 5 was provided, that is, on a hard surface in which the elastic body layer 4 was supported by the substrate layer 5 and whose modulus of elasticity was high.

Example 3

The structure used for animal cells 3 in which a polymer membrane of a thickness of about 50 μm which forms the elastic body layer 4 having a flat surface was adhered to the substrate layer 5 in which a rectangular columnar protrusion 7 having a height of 20 μm and a width of 10 μm was formed was obtained.

Figure 6A:
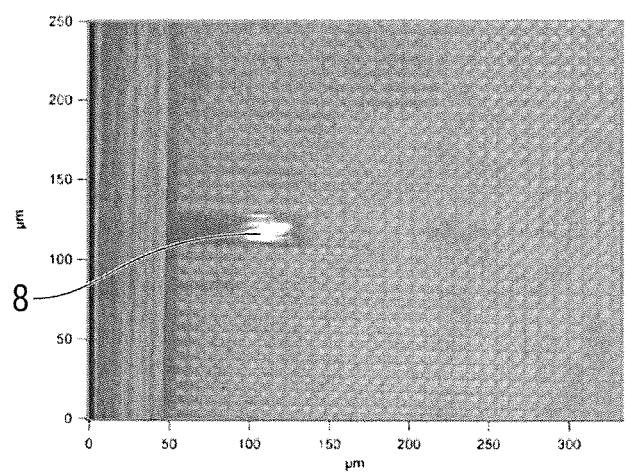
FIG. 6A shows an image obtained by measuring a shape image and a phase image on a polycaprolactone film that is provided on a substrate layer having a grid pattern in an AFM resonance mode in Example 3.
Figure 6B:
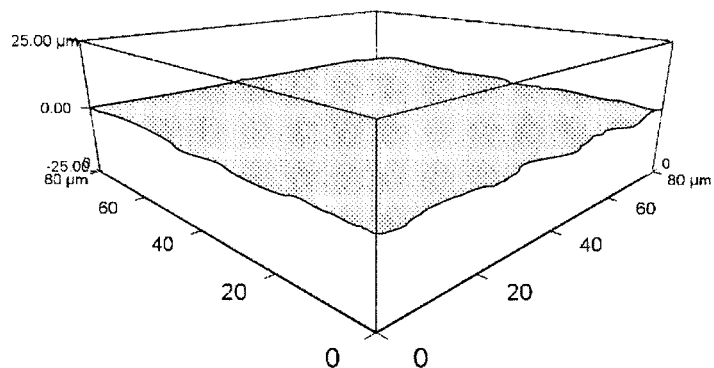
FIG. 6B is a diagram illustrating a shape image of a structure used for animal cells of Example 3 measured in the AFM resonance mode.
Figure 6C:
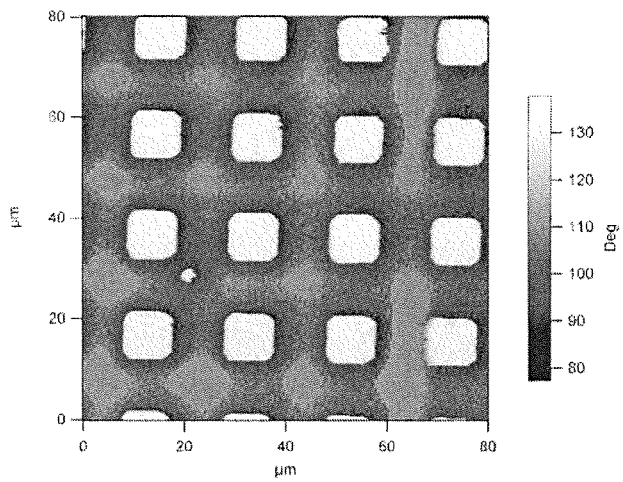
FIG. 6C is a diagram illustrating a phase image of the structure used for animal cells of Example 3 measured in the AFM resonance mode.

As illustrated in FIG. 6A, measurement was performed in the AFM resonance mode. FIGS. 6B and 6C are photographic views of a shape image and a phase image of a membrane surface of the structure used for animal cells 3 obtained in the AFM resonance mode. As illustrated in FIG. 6B, it can be seen that, regardless of the polymer membrane forming the elastic body layer 4 that was almost flat, the phase image of FIG. 6C had clear contrast. In addition, it was confirmed that, even when the three-dimensional shape of the substrate layer 5 had a different pattern, similarly to Example 1 or the like, the animal cells 1 were aggregated at a part in which the peak portion of the substrate layer 5 was provided, that is, on a hard surface whose modulus of elasticity was high (not illustrated).

Example 4

Figure 7:
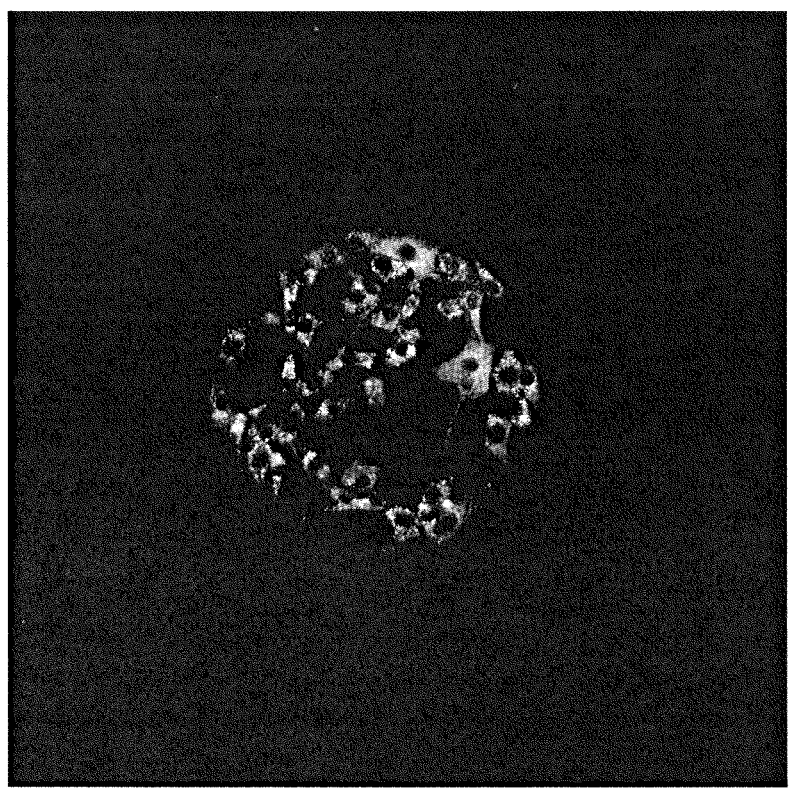
FIG. 7 is a photographic view showing a cell aggregation formed on a flat film in Example 4.

A substrate layer having an erected cylindrical structure of a diameter of 300 μm on a planar surface thereof was prepared. A PCL-containing solution was dropped from above the substrate layer, and a surface of the layer on which the liquid was dropped was left to be horizontal and dried. As a result, the structure used for animal cells 61 having the elastic body layer 4 whose surface was flat was obtained. A thickness of the elastic body layer 4 was 10 to 20 μm on the cylindrical structure, and was 30 to 40 μm in the other part. When NIH3T3 cells were cultured on the flat surface of the obtained structure used for animal cells 61, and forms of the cells were observed. As a result, formation of a circular cell aggregation shown in FIG. 7 was confirmed. Since a position and a size of the cell aggregation were approximately equal to a position and a horizontal direction cross-section (a circle whose diameter is 300 μm) of the cylindrical structure, it was found that the cells were aggregated at a hard surface part that was supported by the substrate layer.

The present invention encompasses the following technical ideas.

(1) A structure used for animal cells that is a structure including an elastic body layer and a substrate layer from the top, and includes a substrate layer portion that supports the elastic body layer and a substrate layer portion that does not support the elastic body layer. The substrate layer or the elastic body layer changes elasticity of a surface of the elastic body layer by a three-dimensional shape having protrusions and recesses thereof.

(2) A structure used for animal cells that is a structure including an elastic body layer and a substrate layer from the top and includes a substrate layer portion that supports the elastic body layer. By changing a thickness of the elastic body layer according to a three-dimensional shape having protrusions and recesses of the substrate layer, elasticity of a surface of the elastic body layer is changed.

(3) The structure used for animal cells according to item (1) or (2), wherein the substrate is a substrate which controls migration, proliferation and differentiation of animal cells.

(4) A method of separating animal cells using the substrate using the structure of item (1) or (2).

(5) A method of adjusting elasticity of a surface of a structure used for animal cells wherein the structure includes an elastic body layer, a substrate layer, a portion of the substrate layer that supports the elastic body layer, and a portion of the substrate layer that does not support the elastic body layer. In the method, elasticity of a surface of the elastic body layer is adjusted due to a three-dimensional shape having protrusions and recesses of the substrate layer or the elastic body layer.

(6) A method of adjusting elasticity of a surface of a structure used for animal cells, wherein the structure includes an elastic body layer, a substrate layer, and a portion of the substrate layer that supports the elastic body layer. In the method, elasticity of a surface of the elastic body layer is adjusted by changing a thickness of the elastic body layer according to a three-dimensional shape having protrusions and recesses of the substrate layer.

(7) In the method of adjusting elasticity of a surface of a structure used for animal cells according to item (5) or (6), elasticity of a surface of the elastic body layer is gradually changed according to a three-dimensional shape having protrusions and recesses of the substrate layer or the elastic body layer, and thus elasticity of the surface of the elastic body layer is adjusted.

REFERENCE SIGNS LIST

1 Animal cell
2 Polymer membrane surface
3, 6, 31, 61, 62 Structure used for animal cells
4 Elastic body layer
5 Substrate layer
51 First substrate layer portion
52 Second substrate layer portion
7 Groove
8 AFM probe
(A) Surface of soft area
(B) Surface of hard area
(C), (E), (G) Elastic body layer portion that is supported

The invention claimed is:

1. A method of separating animal cells, comprising separating animal cells using a structure used for animal cells, wherein the surface elasticity of the structure is changed,
   wherein the structure used for animal cells comprises an elastic body layer and a substrate layer, the elastic body layer having a top side and bottom side where the topside has a flat surface on which animal cells are provided, and the substrate layer having a top side and bottom side,
   wherein the elasticity of the flat surface of the elastic body layer is changed by only partially supporting the bottom side of the elastic body layer, or by changing the thickness of the elastic body layer, and
   wherein
   (a) when the elasticity of the flat surface of the elastic body layer is changed by only partially supporting the bottom side of the elastic body layer, the elastic body layer has a uniform thickness, and the bottom side of the elastic body layer is only partially supported by the substrate layer by discontinuous contact therewith,
   wherein the substrate layer is not uniformly thick and has a three-dimensional shape having protrusions and recesses on the top side, and
   the protrusions support the bottom side of the elastic body layer, and
   the recesses form, with the bottom side of the elastic body, a plurality of channels beneath the bottom side of the elastic body, and the elasticity of the surface of the elastic body layer varies between supported and unsupported portions of the elastic body layer, and
   (b) when the elasticity of the flat surface of the elastic body layer is changed by changing the thickness of the elastic body layer, the substrate layer is uniform in thickness, and
   the elastic body is not uniform in thickness and the bottom side of the elastic body layer is formed in a three-dimensional shape having protrusions and recesses,
   the protrusions contact with the top side of the substrate layer,
   the recesses form, with the top side of the substrate layer, a plurality of channels above the top side of the substrate layer such that the elastic body layer is only partially supported by the top side of the substrate layer by discontinuous contact therewith, and the elasticity of the surface of the elastic body layer varies between supported and unsupported portions of the elastic body layer.

2. The method of separating animal cells according to claim 1,
   wherein the method is used to control migration, proliferation and differentiation of animal cells.

3. The method of separating animal cells according to claim 1, comprising, before the separating step is performed,
   generating the structure used for animal cells wherein the surface elasticity of the structure is changed, and
   providing animal cells on the substrate.

4. The method of separating animal cells according to claim 1, wherein the method includes a step wherein the elastic body layer having the uniform thickness and the flat surface described in (a) is generated by performing spin-coating on a cover glass, wherein the flatness of the flat surface of elastic body layer is provided by the surface of the cover glass by the spin coating.

5. The method of separating animal cells according to claim 1, wherein the elastic body layer is formed from at least one of a polymer material or a rubber material.

6. The method of separating animal cells according to claim 1, wherein crosslinking is not performed when the elastic body layer is formed.

7. The method of separating animal cells according to claim 1, wherein the method includes a step wherein the structure used for animal cells which satisfies (a) is formed by a production method comprising:
   producing an elastic body layer on a cover glass by spin-coating, and providing a substrate layer having a three-dimensional shape having protrusions and recesses on a surface thereof on another cover glass,
   adhering the cover glass on which the elastic body layer is formed to another cover glass so that the elastic body layer faces the surface of the substrate layer, and
   removing the cover glass from the elastic body layer.

8. The method of separating animal cells according to claim 7, wherein the production method further comprises:
   placing a weight directly on the cover glass to which the elastic body layer is provided between the adhering step and the removing step, and
   providing a weight and a washer on the elastic body layer after removing the cover glass from the elastic body layer, and
   removing the weight and the washer from the elastic body layer.

9. The method of separating animal cells according to claim 1, wherein the method includes a step wherein the structure used for animal cells which satisfies (a) is formed by a production method comprising:
   preparing an elastic body layer which has a flat surface and a uniform thickness,
   preparing a substrate layer which has a surface having a three-dimensional shape which includes a first substrate layer portion which corresponds to protrusions, and a second substrate layer portion which corresponds to recesses, and
   placing the elastic body layer on the first substrate layer portion of the substrate layer.

10. The method of separating animal cells according to claim 1, wherein the method includes a step wherein the elastic body layer which is described in (b) is formed by a production method comprising:

applying an elastic material to a substrate having an unevenness on the surface thereof, drying the elastic material without performing a cross-linking step, and peeling off the elastic material from the substrate to form an elastic body layer wherein a bottom side of the elastic body layer is formed in a three-dimensional shape having protrusions and recesses.

11. The method of separating animal cells according to claim 1, wherein the substrate layer is made of glass, a silicon, a plastic, and a metal, or a flexible material having higher hardness than that of the elastic body layer.

* * * * *